(12) United States Patent
Wu

(10) Patent No.: US 8,883,177 B2
(45) Date of Patent: Nov. 11, 2014

(54) PHARMACEUTICAL COMPOSITIONS FOR PARENTERAL ADMINISTRATION

(76) Inventor: Nian Wu, North Brunswick, NJ (US)

( * ) Notice: Subject to any disclaimer, the term of this patent is extended or adjusted under 35 U.S.C. 154(b) by 0 days.

(21) Appl. No.: 13/532,023

(22) Filed: Jun. 25, 2012

(65) Prior Publication Data

US 2013/0004592 A1    Jan. 3, 2013

Related U.S. Application Data

(60) Provisional application No. 61/502,065, filed on Jun. 28, 2011.

(51) Int. Cl.
| | |
|---|---|
| *A61K 9/00* | (2006.01) |
| *A61K 9/16* | (2006.01) |
| *A61K 9/14* | (2006.01) |
| *A61K 47/34* | (2006.01) |
| *A61K 47/26* | (2006.01) |
| *A61K 9/08* | (2006.01) |
| *A61K 31/05* | (2006.01) |
| *A61K 31/337* | (2006.01) |
| *A61K 31/496* | (2006.01) |
| *A61K 31/506* | (2006.01) |
| *A61K 33/24* | (2006.01) |
| *A61K 47/14* | (2006.01) |

(52) U.S. Cl.
CPC ............ *A61K 9/0019* (2013.01); *A61K 9/1617* (2013.01); *A61K 9/141* (2013.01); *A61K 47/34* (2013.01); *A61K 9/1641* (2013.01); *A61K 47/26* (2013.01); *A61K 9/08* (2013.01); *A61K 31/05* (2013.01); *A61K 31/337* (2013.01); *A61K 31/496* (2013.01); *A61K 31/506* (2013.01); *A61K 33/24* (2013.01); *A61K 47/14* (2013.01)
USPC ........................................ 424/400

(58) Field of Classification Search
CPC ....... A61K 9/0019; A61K 9/08; A61K 9/141; A61K 9/1617; A61K 9/1641; A61K 47/14; A61K 47/26; A61K 47/36
See application file for complete search history.

(56) References Cited

U.S. PATENT DOCUMENTS

| | | |
|---|---|---|
| 6,309,633 B1 | 10/2001 | Ekwuribe et al. |
| 2003/0215395 A1 | 11/2003 | Yu et al. |

(Continued)

FOREIGN PATENT DOCUMENTS

| | | |
|---|---|---|
| RU | 2327702 C2 | 6/2008 |
| RU | 2359698 | 6/2009 |

(Continued)

OTHER PUBLICATIONS

Zalipsky S et al: "Poly(Ethylene 1-15 Glycol)-Grafted Liposomes With Oligopeptide or Oligosaccharide Ligands Appended to the Termini of the Polymer Chains", Bioconjugate Chemistry, ACS, Washington, DC, US, vol. 8, No. 2, Mar. 1, 1997, pp. 111-118, XP000858875, ISSN: 1043-1802, DOI: 10.1021/BC9600832 figure 1.

(Continued)

*Primary Examiner* — Bethany Barham
(74) *Attorney, Agent, or Firm* — Steve Witters; Witters & Associates

(57) ABSTRACT

The invention comprises various aqueous PEG-carbohydrate-lipid based formulations of pharmaceutical active ingredients including compositions for intravenous injections. This invention relates to methods and compositions for improving solubility and the safety profile of pharmaceutical compounds. More particularly, the present invention relates to employing PEG-carbohydrate-lipid conjugates for formulating drug compositions having increased solubility or dispersivity and enhanced stability.

11 Claims, 2 Drawing Sheets

(56) References Cited

U.S. PATENT DOCUMENTS

| | | | |
|---|---|---|---|
| 2007/0082838 A1* | 4/2007 | De et al. .................... | 514/2 |
| 2010/0026817 A1 | 2/2010 | Ryan et al. | |
| 2010/0210518 A1* | 8/2010 | Keller et al. ................ | 514/11 |
| 2010/0260817 A1* | 10/2010 | Slobodkin et al. .......... | 424/426 |

FOREIGN PATENT DOCUMENTS

| | | |
|---|---|---|
| WO | WO0024438 | 5/2000 |
| WO | WO0078302 | 12/2000 |
| WO | WO2006050072 | 5/2006 |
| WO | WO2010085347 | 7/2010 |
| WO | WO2010107487 | 9/2010 |
| WO | WO2010141069 | 12/2010 |
| WO | WO2011005980 | 1/2011 |

OTHER PUBLICATIONS

Yiguang Wang et al., "Pegylated Phospholipids-Based Self-Assembly with Water Soluble Drugs", Pharmaceutical Research, 2010, vol. 27, No. 2, pp. 361-370, Abstract, Fig. 1, Chemical Structures C, A, B, p. 362, col. 1, paragraphs 1, 2, col. 2, last paragraph, p. 363, col. 2, last paragraph, p. 364, col. 1, first paragraph.

* cited by examiner

PHARMACEUTICAL COMPOSITIONS FOR PARENTERAL ADMINISTRATION

CROSS-REFERENCE TO A RELATED APPLICATION

The subject application claims priority to U.S. provisional application Ser. No. 61/502,065, filed on Jun. 28, 2011, the entire contents of which are hereby incorporated by reference.

FIELD OF THE INVENTION

This invention relates to methods and compositions for improving solubility and the safety profile of pharmaceutical compounds. More particularly, the present invention relates to employing Polymer-carbohydrate-lipid conjugates, such as PEG-carbohydrate-lipid conjugates, for formulating drug compositions having increased solubility or dispersivity and enhanced stability.

BACKGROUND OF THE INVENTION

Delivery of hydrophobic drug compounds to the site of action is an ongoing challenge in clinical research. It has been reported that 60-90% of new chemical entities in clinical and development are water insoluble or poorly soluble [A. M. Thayer (2010), Chemical & Engineering News, 88(22): 13-18; C. A. Lipinski, J Pharmacol Toxicol Method 44 (2000) 235-2490 and N. Gursoy and S. Benita, Biomed. Pharmacother. 58 (2004) 173-182]. For example, Propofol is insoluble in water and is only slightly soluble in solutions having solubilizers commonly used in preparing parenteral formulations such as propylene glycol, glycerin and PEG 400. Cyclodextrins, drug-lipid complexes, liposomes, and other solubilizing agents such as Cremophor® and various PEG-lipid conjugates have been tested as the delivery vehicles for Propofol. However, little or substantially no significantly improvement in solubility and stability profiles may be achieved in these vehicles. What is needed are new compositions and methods for formulating poor water soluble drugs in various parenteral dosage forms.

SUMMARY OF THE INVENTION

In at least one aspect of the present disclosure, a pharmaceutical composition for parenteral administration of a pharmaceutical active ingredient is provided. The composition comprises: a) an aqueous solution or mixture; b) a pharmaceutical active ingredient; and c) a solubility enhancer comprising a Polymer-carbohydrate-lipid represented by at least one of chemical structures a) and b), wherein a) and b) are:

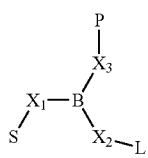

(a)

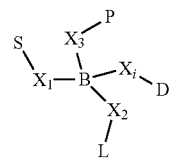

(b)

wherein: $X_1$, $X_2$, $X_3$ and $X_i$ are the same or different linking groups; B is a central backbone; L is a lipid; S is carbohydrate; P is PEG; and D is lipid, carbohydrate or polymer.

In at least one other aspect of the present disclosure, a pharmaceutical composition for parenteral administration of a pharmaceutical active ingredient is provided. The composition comprises: i) an aqueous solution or mixture; ii) a solubility enhancer comprising at least one Polymer-carbohydrate-lipid; and iii) a pharmaceutical active ingredient.

In at least one aspect of the present disclosure, a process for making a pharmaceutical composition for parenteral administration of a pharmaceutical active ingredient is provided. The process comprises the steps of: adding an aqueous solution of PEG-carbohydrate-lipids to a vessel; adding a pharmaceutical active ingredient in liquid or Slurry form to the vessel; mixing until the pharmaceutical active ingredient is visually dispersed in the aqueous solution of PEG-carbohydrate-lipids; adding pre-dissolved excipients to the vessel; and mixing until a homogenous solution is achieved.

BRIEF DESCRIPTION OF THE INVENTION

The invention comprises various aqueous and PEG-carbohydrate-lipid based formulations of poorly water soluble drugs including compositions for parenteral preparations such as intravenous injection. In one aspect the invention comprises a solution of lipophilic compound and PEG-carbohydrate-lipid (s) to enhance the solubility or dispersivity of lipophilic compounds in aqueous solutions.

In at least one aspect of the present disclosure, a pharmaceutical composition for parenteral administration of a pharmaceutical active ingredient is provided. The composition comprises: an aqueous solution or mixture; a solubility enhancer comprising at least one polymer-carbohydrate-lipid; and a pharmaceutical active ingredient.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Figure 1:
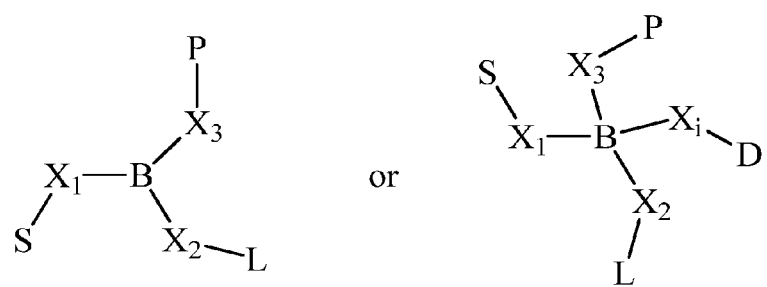
FIG. 1 shows a representation of the chemical structures of Lipid-carbohydrate-PEG conjugates.

Embodiments of the present invention are described herein in the context of lipid-carbohydrate-polymer conjugates for increasing the solubility and enhancing the delivery of lipophilic drug molecules. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions may need be made in order to achieve specific goals, such as compliance with application and business related constraints, and that these specific goals may vary from one implementation to another and from one developer to another. However, development and implementation of the disclosed may be a routine undertaking of engineering for those of ordinary skill in the art having the benefit of this disclosure.

U.S. patent application Ser. Nos. 13/364,967 and 13/354,726, which are hereby incorporated by reference, may teach the formation of spontaneous liposomes by employing certain lipid-carbohydrate-polyethleneglycol (LCP) conjugates. They may describe how to prepare the PEG-carbohydrate-lipid conjugates and its applications by simply adding the conjugate to an aqueous solution. It has been demonstrated that LCPs may be useful for solubilizing hydrophobic drugs without the formation of liposomes or microemulsions.

Over last three decades, some of promising drug carriers that have been investigated in systemic delivery systems includes liposomes, polymeric nanoparticles, polymeric micelles, ceramic nanoparticles and dendrimers (Cherian et al. Drug. Dev. Ind. Pharm, 26: (2000) 459-463; Lian and Ho. J. Pharm. Sci, 90 (2001) 667-680; Adams et al. Pharm. Sci, 92 (2003) 1343-1355; Na et al. Eur. J. Med. Chem., 41 (2006) 670-674; Kaur et al. J. Control. Rel, 127 (2008) 97-109). Systemic drug delivery may be achieved by intravenous or intraperipheral injection and therefore is non-invasive. The drugs may be administered repeatedly as needed. However, in order to achieve therapeutic concentrations at the target site, systemic administration may require large dosages with relatively high vehicle contents which may cause side effects such as allergic reactions ["Cremophor-based paclitaxel 'chemo' drug triggers fatal allergic reactions," The Medical News. 9 Jun. 2009].

Polyethylenglycol (PEG) is widely used as a water soluble carrier for polymer-drug conjugates. PEG may undoubtedly be the most studied and applied synthetic polymer in the biomedical field [Duncan, R. Nature Rev. Drug Discov. 2003, 2, 347-360]. As an uncharged, water-soluble, nontoxic, non-immunogenic polymer, PEG may be an ideal material for biomedical applications. Covalent attachment of PEG to biologically active compounds is often useful as a technique for alteration and control of biodistribution and pharmacokinetics, minimizing toxicity of these compounds [Duncan, R. and Kopecek, J., Adv. Polym. Sci. 57 (1984), 53-101]. PEG possesses several beneficial properties: very low toxicity [Pang, S. N. J., J. Am. Coil. Toxicol, 12 (1993), 429-456], excellent solubility in aqueous solutions [Powell, G. M., Handbook of Water Soluble Gums and Resins, R. L. Davidson (Ed.), Ch. 18 (1980), MGraw-Hill, New York], and extremely low immunogenicity and antigenicity [Dreborg, S, Crit. Rev. Ther. Drug Carrier Syst., 6 (1990), 315-365]. The polymer is known to be non-biodegradable, yet it is readily excretable after administration into living organisms. In vitro study showed that its presence in aqueous solutions has shown no deleterious effect on protein conformation or activities of enzymes. PEG also exhibits excellent pharmacokinetic and biodistribution behavior. [Yamaoka, T., Tabata, Y. and Ikada, Y., J. Pharm. Sci. 83 (1994), 601-606].

When used as a delivery vehicle, polymer-lipid conjugates may have the capacity to improve the pharmacology profile and solubility of lipophilic drugs. The novel polymer-carbohydrate-lipid conjugates disclosed in the earlier inventions may also provide other potential advantages over conventional polymer-lipids, i.e., PEG-lipids, such as minimizing side effects and toxicities associated with therapeutic treatments.

The important role of sugars in many specific interactions in living systems is well recognized. Large molecular weight carriers such as proteins or liposomes may be modified with sugars for specific drug delivery [Monsigny M, Roche A C, Midoux P and Mayer R., Adv Drug Delivery Rev., 14 (1994): 1-24; Palomino E. Adv Drug Delivery Rev., 13 (1994)311-323]. Lipid-sugar particles have been used for drug delivery to the brain for providing prolonged duration local anesthesia when injected at the sciatic nerve in rats [Kohane D S, Lipp M, Kinney R., Lotan N, Langer R., Pharm. Res. 17 (2000) 1243-1249]. Since sugar-lipids are composed of materials that occur naturally in the human body suggests potential advantages over some other polymer-based controlled-release terms of biocompatibility [Kohane D S, Lipp M, Kinney R, Anthony D, Lotan N, Langer R., J. Biomed. Mat. Res. 59 (2002) 450-459; Menei P, Daniel V, Montero-Menei C, Brouillard M, Poupard-Barthelaix A, Benoit J P., Biomaterials, 14 (1993) 470-478]. Lipid-sugars may have a good biocompatibility as shown by the results of the in vitro and in vivo studies [Kohane D S, Lipp M, Kinney R, Anthony D, Lotan N, Langer R., J. Biomed. Mat. Res. 59 (2002) 450-459].

A preferred embodiment of the present disclosure may comprise an aqueous-based, injectable drug solution including and not limited to oleoyltri-ethylenetetramine-polyethyleneglycol lactobionate (OTL-PEG) or oleoyldiethylenetetramine-dodecaethylene glycol lactobionate (ODL-PEG). In at least one aspect of the present disclosure, the solution includes a drug molecule in concentrations ranging from 0.05 mg/mL to 50 mg/mL and the ratio of PEG-lipid to the drug ranges from 0.2 to 25. In at least one other aspect of the present disclosure, the concentration of drug molecule ranges from 0.5 mg/mL to 50 mg/mL. In at least one additional aspect of the present disclosure, the concentration of drug molecule ranges from 0.5 mg/mL to 10 mg/mL and the percent of PEG-carbohydrate-lipid ranges from 0.5 to 10 (w/v) of the total solution.

Further aspects of the present disclosure may provide aqueous, injectable drug solutions in which the diluent consists of 0.5 to 25 percent (w/v) of the PEG-carbohydrate-lipid and 75 to 99.5 percent (v/v) of water or a buffer or saline or dextrose solution. Also preferable are aqueous, injectable drug solutions of this invention in which 85 to 99 percent (v/v) of the total solution is water or a buffer or saline or dextrose solution.

In at least one aspect of the present disclosure, aqueous injectable drug solutions according to the present invention comprise lipophilic drug compound in LCP lipids including and not limited to OTL-PEG or ODL-PEG plus aqueous media at concentrations of a drug ranging from 0.5 mg/mL to 50 mg/mL, 0.5 to 25 percent (w/v) of PEG-carbohydrate lipid, and 75 to 99.5 percent (v/v) water, wherein the concentration of drug in the combined solution ranges from 0.5% to 5%.

The aqueous injectable drug solutions of the present disclosure may be administrated by bolus injection or by infusion. Infusion may be preferable for such solutions where the concentration of drug in is greater than 0.01 mg/mL. In case of an infusion, the length of an infusion may be preferable 30 minutes to 6 hours and may not be more than 24 hours.

Aspects of the present disclosure involve solubilizing a drug or drugs, by using one or more amphipathic PEG conjugates. A combination of LCPs and polysorbates may be preferred solubilizing agents, in which acyl chains comprise the lipophilic portion of the conjugate. Examples of LCPs are shown in FIG. 1.

A branched PEG-carbohydrate-lipid may also be an excellent solubilizing agent, in which the polymer comprises the more than single PEG chains of the conjugate. Similarly, branched-PEG-carbohydrate-lipids may also be used as solubilizing agents. As with LCP solubilizing agents, these compounds typically are waxy solid or semisolids at the temperature of solubilization, these PEG-carbohydrate-lipids typically have melting points above about 25 degrees Centigrade. Such solubilizing agents may also be used to prepare IV formulations and oral or topical liquids.

A first step for solubilization may comprise combining the drug compound(s), with an amphipathic PEG conjugate(s) which may be semisolid or solid at the temperature of solubilization. For formulating a drug solution at room temperature (which may be preferred), a concentrated solution of a conjugate may be desired. Such solubilization may be done by first adding the liquid form of a drug to the concentrated solution of the conjugates. The aqueous solution may be further diluted with water or a buffer. Alternatively, the drug compound(s) may be pre-dissolved in a small amount of acid, base or alcohol, then mix with the PEG-carbohydrate-lipids in aqueous solution.

By performing solubilization at elevated temperatures, conjugates with higher melting temperatures may be used as solubilizing agents. When forming aqueous solutions, the aqueous solution may also be preferably added at an elevated temperature.

The LCP lipids shown in Table 1 may be suitable for use in various aspects of the present disclosure. LCPs with oxy or amide or succinyl linkers (X=oxygen or carbonyl or succinyl) may be preferred, though LCPs with other linkers may be used.

The lipid-carbohydrate polymer conjugates shown in FIG. 1 may be suitable for use in various aspects of the present disclosure. Where $X_1$, $X_2$, $X_3$ and $X_i$ are the same or different linking groups; "L" is a lipid; "S" is carbohydrate; "P" is a polymer; and "D" is lipid (the same or different than "L") or carbohydrate (the same or different than "S") or polymer (the same or different than "P").

Backbone (B) may comprise glycerol or glycerol-like analogues or linear amines (tri- or tetra-amines) or amino acids having three available binding sites; where the lipid (L) may comprise carboxylic acids including and not limited to diacylglycerol or fatty acids or bile acids; sugar (C) may comprise a carbohydrate including monosaccharides or disaccharides or oligosaccharides; $X_1$, $X_2$ and $X_3$ and $X_i$ are the same or different linkers and X represents an oxy or single or replicate linkers or combination of two or more molecules in between the backbone and one of functional groups. The General Structure is meant to include all racemers or structural isomers of the structure, as they may be functionally equivalent. The PEG chain (P) may be a single PEG or a branched PEG chains consisting of 5 to 45 subunits. There may be a terminal group (R) on the PEG chain which may comprise a wide variety of chemical moieties. In at least one aspect of the present disclosure, R has a molecular weight of less than about 650. D may comprise a secondary sugar or lipid or PEG. The Lipid-carbohydrate-PEG conjugates may be useful for applications other than liposomes, e.g., as a solvent.

If a terminal group is attached to the PEG chain in FIG. 1, it may comprise a wide variety of chemical moieties. Such moieties may have a molecular weight of less than 650. Such moieties include —$NH_2$, —COOH, —$OCH_2CH_3$, —$OCH_2CH_2OH$, —COCH=$CH_2$, —$OCH_2CH_2NH_2$, —$OSO_2CH_3$, —$OCH_2C_6H_6$, —$OCH_2COCH_2CH_2COONC_4H_4O_2$, —$CH_2CH_2$=$CH_2$, $C_{10}H_{16}N_2O_3S$ and —$OC_6H_6$. The terminal group may be a functional group that facilitates linking of therapeutic or targeting agents to the surface of lipid vesicle aggregates. Amino acids, amino alkyl esters, biotins, maleimide, diglycidyl ether, maleinimido propionate, methylcarbamate, tosylhydrazone salts, azide, propargyl-amine, propargyl alcohol, NHS esters (e.g., propargyl NHS ester, NHS-biotin, sulfo-NHS-LC-biotin, or NHS carbonate), hydrazide, succinimidyl ester, succinimidyl tartrate, succinimidyl succinate, and toluenesulfonate salt may be useful for such linking. Linked therapeutic and targeting agents may include Fab fragments (fragment antigen-binding), cell surface binding agents, and the like. Additionally, the terminal group may include functional cell-targeting ligands such as folate, transferrin and molecules such as monoclonal antibodies, ligands for cellular receptors or specific peptide sequences may be attached to the liposomal surface to provide specific binding sites. The terminal group may be neutral or include either negatively or positively charged head-groups such as decanolamine, octadecylolamine, octanolamine, butanolamine, dodecanolamine, hexanolamine, tetradecanolamine, hexadecanolamine, oleylamine, decanoltrimethylaminium, octadecyloltrimethylaminium, octanoltrimethyl-aminium, butanoltrimethylaminium, dodecanoltrimethylaminium, hexanoltrimethylaminium, tetradecanoltrimethylaminium, hexadecanoltrimethylaminium, oleyltrimethylaminium, for example. Other useful R groups include alkyl groups such as alkoxy moieties, amino acids, and sugars including monosaccharides, disaccharides, trisaccharides and the oligosaccharides—containing 1, 2, 3, and 4 or more monosaccharide units respectively. Additionally, targeting moieties such as antibody fragments and vitamins may also be used as R groups. Generally, the R group may be highly soluble in water. The molecular weight of the R group may be less than about 650, and for most applications the R group may be easily polarized, in order to increase the binding and interaction with proteins at the targeted sites.

TABLE 1

PEG-lipid (Lipid-carbohydrate-polyethyleneglycols)

| Shorthand name | Name |
|---|---|
| MAGC-PEGs | monoacylglycerol-carbohydrate-polyethylene glycols |
| MAPC-PEGs | monoacylpolyamine-carbohydrate-polyethylene glycols |
| MAAC-PEGs | monoacylamino acid-carbohydrate-polyethylene glycol |
| ODL-TrpPEGs | oleoyldiethylenetriamine-tryptophanyl PEG |
| LOS-PEGs | N-lactobionyloleoyl-mPEG serinate |
| LOS-bioPEGs | N-lactobionyloleoyl-biotinylated PEG serinate |
| OAPDL-11 | oleoyl-N-(3-aminopropyl)propane-1,3-diamine-Undecaethylene glycol methyl ether Lactobionate |
| GDODL-12: | dioleoylglyceroldiethylenetriamine-monomethoxyl dodecaethylene glycol ether lactobionate |
| GMODL-12 | dimyristoylglycerol diethylenetriamine-monomethoxyl dodecaethylene glycol ether lactobionate |
| GML-12 | myristoylglycerol-dodecaethylene glycol lactobionate |
| GOL-12 | oleoylglycerol-dodecaethylene glycol lactobionate |
| MDTL-12 | myristoyldiethylenetetramine-dodecaethylene glycol lactobionate |
| ODL-12 | oleoyldiethylenetriamine-dodecaethylene glycol lactobionate |
| ODL-15 | oleoyldiethylenetriamine-pentadecaethylene glycol lactobionate |

TABLE 1-continued

PEG-lipid (Lipid-carbohydrate-polyethyleneglycols)

$$\begin{array}{c} \text{PEG}_n\text{—R} \\ X_2\text{—Backbone—}X_1 \\ \text{Sugar} \quad \quad X_3 \\ \text{Lipid} \end{array}$$

and/or $$\begin{array}{c} \text{Lipid} \\ X_2\text{—Backbone—}X_1 \\ \text{Sugar} \quad \quad X_3 \\ R\text{—PEG}_n \end{array}$$

| Shorthand name | Name |
|---|---|
| ODTL-12 | oleoyldiethylenetetramine-dodecaethylene glycol lactobionate |
| ODTL-15 | oleoyldiethylenetetramine-pentadecaethylene glycol lactobionate |
| MTL-12 | myristoyltriehylenetetramine-dodecaethylene glycol lactobionate |
| OTL-12 | oleoyltriethylenetetramine-dodecaethylene glycol lactobionate |
| OTL-15 | oleoyltriethylenetetramine-pentadecaethylene glycol lactobionate |
| GDODL-12 | dioleoylglycerol-diethylenetriamine-monomethoxyl polyethylene glycol ether lactobionate |
| OAPEL-PEG | oleoyl(aminopropylamino)ethanoyl-mPEG Lactobionate |
| LOS-bioPEG | N-lactobionyloleoyl-biotinylated PEG Serinate |
| LOL-bioPEG | N-lactobionyloleoyl-biotinylated PEG Lycinate |
| DCAL-PEG | N-desoxycholylaspartate-mPEG lactobionate |
| OAL-mPEG | oleoylaminopropanediol-mPEG lactobionate |
| OAL-bioPEG | oleoylaminopropanediol-biotinylated PEG lactobionate |
| ODL-ThrPEG | oleoyldiethylenetriamine-threoninyl PEG lactobionate |
| ODL-bioPEG | oleoyldiethylenetriamine-biotinylated PEG lactobionate |
| ODL-PEG | oleoyldiethylenetriamine-PEG lactobionate |

$X_1$, $X_2$ and $X_3$ represent linkers which may be oxy or thiol or carbonyl, amino or succinyl or the like may not be distinguished in the following name and detailed in the preceding sections. $X_1$, $X_2$ and $X_3$ may be the same or different. The number of subunits in the PEG polymer ranges from 6 to 16.

Mixtures of PEG-carbohydrate-lipids may be used in the present disclosure in the place where combinations of PEG-carbohydrate-lipids are used, the properties of the lipid mixture (e.g., melting point or average size of the PEG chain) may be calculated by known methods or determined empirically.

The manufacture of parenteral solution may comprise first adding a drug to a concentrated PEG-carbohydrate-lipid solution and mixing until homogenous, which may be accomplished at room temperatures. Next, premixed aqueous integrants may be added to the lipid-drug mixture and mixed until a homogenous solution is obtained. The solution may then be filtered for sterility while maintaining an overlay of sterile-filtered nitrogen during the process. Appropriate volumes of the solution may be filled into ampules and sealed using aseptic technique. Sterile conditions may be maintained throughout the filtering, filling, and sealing operations in accordance with standard manufacturing procedures for injectables. While the formulated product may be stable at room temperature, it may be preferably stored under refrigeration for extended shelf life.

A preservative may be desired when the sterile-filtered process is prevented by high concentrations of PEG-carbohydrate-lipids, the possible preservatives may be selected from a group of antimicrobial agents consisting of benzyl alcohol, chlorobutanol, methylparaben, propylparaben, phenol, ethylenediaminetetraacetic acid, and m-cresol.

In one aspect of the present disclosure, a pharmaceutical composition for administration by intravenous injection is provided. The composition comprises an aqueous solution; a PEG-carbohydrate-lipid or combination of PEG-carbohydrate-lipids; and a drug at a concentration between about 0.05 mg/mL and about 50 mg/mL. The weight ratio of the PEG-carbohydrate-lipids to the drug may be between about 0.2 and 25. The average MW of PEG chains in the PEG-carbohydrate-lipid or mixture of PEG-carbohydrate-lipids may be less than about 1500. The concentration of a drug may preferably be between about 0.2 mg/ml to 50 mg/ml. The concentration of PEG-carbohydrate-lipids (s) may preferably be between about 0.5 to 25 percent (w/v) of the total solution.

In another aspect, the disclosure provides a method of making a pharmaceutical composition suitable for administration by intravenous injection. The method comprises mixing a PEG-carbohydrate-lipid or combination of PEG-carbohydrate-lipids with a drug and adding an aqueous solution while mixing to create a suspension. The final concentration of the drug may preferably be between about 0.05 mg/ml and about 50 mg/ml. The weight ratio of the total PEG-lipid to the drug compound may preferably be between about 0.2 and 25. The average MW of PEG chains in the PEG-carbohydrate-lipids or combination of PEG-carbohydrate-lipids may preferably be less than about 1500. The method may further comprise sealing the aqueous suspension in a sterile container or adding antimicrobial preservatives.

In another aspect of the present disclosure, a method of treating a disease in a mammal is provided. The method comprises preparing a composition comprising an aqueous solution, a PEG-carbohydrate-lipid or combination of PEG-carbohydrate-lipids, and drug compound at a concentration between about 0.05 mg/mL and about 50 mg/mL. The weight ratio of the PEG-carbohydrate-lipids to the drug may be between about 0.2 and 25. The composition may be administered to the mammal intravenously. The average MW of single PEG chains in the PEG-carbohydrate-lipid or combination of PEG-carbohydrate-lipids is preferably less than about 1500. The concentration of drug may be between about 0.2 mg/mL to 25 mg/mL. The concentration of PEG-carbohydrate-lipids may be between about 0.5 to 25 percent (w/v) of the total solution. The composition may further comprise antimicrobial preservatives, where the concentration of antimicrobial preservatives may be between about 0.1 to 2%. The disease being treated may be a cancer or a fungal infection, for example. The method may also be used to provide for general anesthesia for surgical procedures or where hypnotic agents are desired.

The following examples intend to further illustrate the practice of the present invention.

EXAMPLE 1

Preparation of Propofol Solution for Injection

Figure 3:
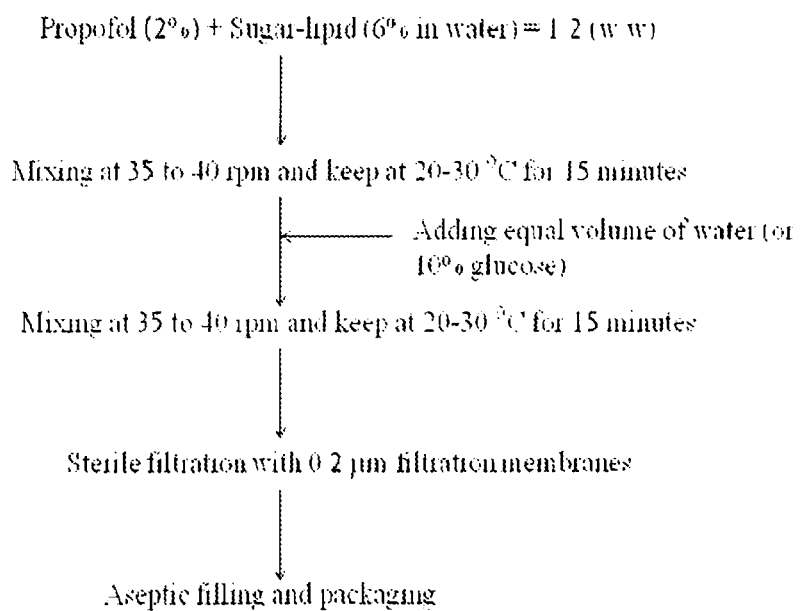
FIG. 3 schematically shows a manufacturing flow chart for Propofol Solution for Injection.

A propofol solution suitable for intravenous delivery was prepared as described in FIG. 3, showing Scheme 1.

Scheme 1, FIG. 3, shows a manufacturing flow chart for Propofol Solution for Injection.

An aqueous solution of PEG-carbohydrate-lipids was added to a vessel equipped with a mixer propeller. The drug substance was added with constant mixing. Mixing was continued until the drug is visually dispersed. Pre-dissolved excipients in water were slowly added to the vessel with adequate mixing. Mixing continued until a homogenous solution was achieved. Sterile conditions should be maintained throughout the process for producing clinical supplies. A sample formulation is described in Table 2.

TABLE 2

| Ingredient | mg/mL |
| --- | --- |
| Propofol | 10.0 |
| PEG-carbohydrate-lipid | 30 |
| Glucose[1] | 50 |
| Purified Water | qs 1 mL |

[1]optional

PEG-carbohydrate-lipid may be selected from Table 1, where n=8 or higher (i.e., the molecular weight of the PEG chain is greater than about 350) or lipid-carbohydrate-PEG, where PEG chain contains 8 to 16 subunits. The targeted pH is in a range of 4.0 to 7.5. Diluted NaOH (i.e., 10N) or HCl solution (i.e., 6N) may be used to adjust pH if necessary.

EXAMPLE 2

Preparation of Propofol Solution for Injection

A propofol solution suitable for intravenous delivery of propofol was prepared the same as in Example 1. A concentrated PEG-carbohydrate-lipid was charged to a vessel equipped with a mixer propeller. The drug substance was added with constant mixing. Mixing continued until the drug was visually dispersed in the lipid solution. Pre-dissolved excipients in water were slowly added to the vessel with adequate mixing. Sterile conditions should be maintained throughout the process for producing clinical supplies. Mixing continued until fully a homogenous solution was achieved. A sample formulation is described in Table 3.

TABLE 3

| Ingredient | mg/mL |
| --- | --- |
| Propofol | 10.0 |
| PEG-carbohydrate-lipid | 30.0 |
| Sodium Chloride | 9.0 |
| Sodium Hydroxide | See below |
| Hydrochloric Acid | See below |
| Purified Water | qs 1 mL |

The lipid-carbohydrate-PEG may be selected from Table 1, where PEG chain contains between 8 to 16 subunits. Sodium hydroxide was used to prepare a 10% w/w solution in purified water. The targeted pH was in a range of 4.0 to 7.5. The NaOH solution or HCl (6N) was used to adjust pH as necessary.

EXAMPLE 3

Preparation of Propofol Solution or Suspension for Injection

A propofol solution suitable for intravenous delivery of propofol was prepared the same as in Example 1. A concentrated solution of PEG-carbohydrate-lipid was charged to a vessel equipped with a mixer propeller. The drug substance was added with constant mixing. Mixing continued until the drug was visually dispersed in the lipid. Pre-dissolved excipients in water were slowly added to the vessel with adequate mixing. Mixing continued until fully a homogenous solution was achieved. Sterile conditions should be maintained throughout the process for producing clinical supplies. A sample formulation is described in Table 4.

TABLE 4

| Ingredient | mg/mL |
| --- | --- |
| Propofol | 10.0 |
| PEG-carbohydrate-lipid | 15.0 |
| Sodium Chloride | 9.0 |
| Sodium Hydroxide | See below |
| Hydrochloric Acid | See below |
| Sodium Benzoate | 20.0[1] |
| Purified Water | qs 1 mL |

[1]preservative is not needed if sterile-filtered is used.

The PEG-carbohydrate-lipid may be selected from Table 1, where PEG chain contains 8 to 16 subunits. Sodium hydroxide was used to prepare a 10% w/w solution in purified water. The targeted pH was in a range of 4.0 to 7.5. The NaOH solution or HCl (6N) was used to adjust pH as necessary.

EXAMPLE 4

Cisplatin IV Injectable Solution

The IV solution is prepared as in Example 1. A sample formulation is described in Table 5.

TABLE 5

| Ingredient | mg/mL |
| --- | --- |
| Cisplatin | 20.0 |
| PEG-carbohydrate-lipid | 20.0 |
| Sodium Chloride | 9.0 |
| Sodium Hydroxide | See below |
| Hydrochloric Acid | See below |
| Purified Water | qs 1 mL |

The PEG-carbohydrate-lipid may be selected from Table 1, where PEG chain contains between 8 to 16 subunits. Sodium hydroxide was used to prepare a 10% w/w solution in purified water. The targeted pH was in a range of 4.0 to 7.5. The NaOH or HCl (6N) solution was used to adjust pH as necessary.

EXAMPLE 5

Docetaxel IV Injectable Solution

The drug substance was charged into a vessel equipped with a mixer propeller. Dehydrated alcohol was added with constant mixing. Mixing continued until the drug was visually disappeared in the Alcohol. Pre-dissolved lipid and excipients in water were slowly added to the vessel with adequate mixing. Mixing continued until fully a homogenous solution was achieved. Sterile conditions should be maintained throughout the process for producing clinical supplies. A sample formulation is described in Table 6.

TABLE 6

| Ingredient | mg/mL |
| --- | --- |
| Docetaxel | 10.0 |
| PEG-carbohydrate-lipid | 25 |
| Dehydrated Alcohol | 10.0 |
| Sodium Chloride | 9.0 |
| Sodium Hydroxide | See below |
| Hydrochloric Acid | See below |
| Purified Water | qs 1 mL |

The PEG-carbohydrate-lipid may be selected from Table 1, where PEG chain contains 8 to 16 subunits. Sodium hydroxide was used to prepare a 10% w/w solution in purified water.

The targeted pH was in a range of 4.0 to 7.5. The NaOH or HCl (6N) solution was used to adjust pH as necessary.

EXAMPLE 6

Paclitaxel IV Injectable Solution

The IV solution was prepared as in Example 5, except that the dehydrated alcohol contained 5% of sodium hydroxide (v/v). A sample formulation is described in Table 7.

TABLE 7

| Ingredient | mg/mL |
|---|---|
| Paclitaxel | 12.0 |
| PEG-carbohydrate-lipid | 30.0 |
| Dehydrated Alcohol | 10.0 |
| Sodium Chloride | 9.0 |
| Sodium Hydroxide | See below |
| Hydrochloric Acid | See below |
| Purified Water | qs 1 mL |

The PEG-carbohydrate-lipid may be selected from Table 1, where PEG chain contains 8 to 16 subunits. Sodium hydroxide was used to prepare a 10% w/w solution in purified water. The targeted pH was in a range of 4.0 to 7.5. The NaOH or HCl (6N) solution was used to adjust pH as necessary.

EXAMPLE 7

Triazole Fungicide IV Injectable Solution or Suspension

The IV solution was prepared as in Example 5. A sample formulation is described in Table 8.

TABLE 8

| Ingredient | mg/mL |
|---|---|
| Active | 10.0 |
| PEG-carbohydrate-lipid | 30.0 |
| Dehydrated alcohol | 20.0 |
| Sodium Hydroxide | See below |
| Hydrochloric Acid | See below |
| Sodium Benzoate | 20.0 |
| Purified Water | qs 1 mL |

The active is voriconazole or posaconazole. PEG-carbohydrate-lipid may be selected from Table 1, where PEG chain contains 8 to 16 subunits. Sodium hydroxide was used to prepare a 10% w/w solution in purified water. The targeted pH was in a range of 4.0 to 7.5. The NaOH or HCl (6N) solution was used to adjust pH as necessary.

EXAMPLE 8

Pharmacokinetic Profile of Propofol formulations

Groups of three male mice (B6D2F1, 4 weeks old and weights of 20 to 28 grams were used for the studies. Pharmacokinetics (PK) were performed on heparinized mouse plasma samples obtained typically at after the bolus IV injection at 1, 3, 8, 12, 15, 20, 30, 45 and 60 minutes for Propofol. Samples were analyzed using a HPLC-MS method. To determine the level of the drug, the drug was first isolated from plasma with a sample pre-treatment. Acetonitrile were used to remove proteins in samples. An isocratic HPLC-MS/MS method was then used to separate the drugs from any potential interference. Drug levels were measured by MS detection with a multiple reaction monitoring (MRM) mode. PK data was analyzed using the WinNonlin program (ver. 5.3, Pharsight) compartmental models of analysis.

Figure 2:
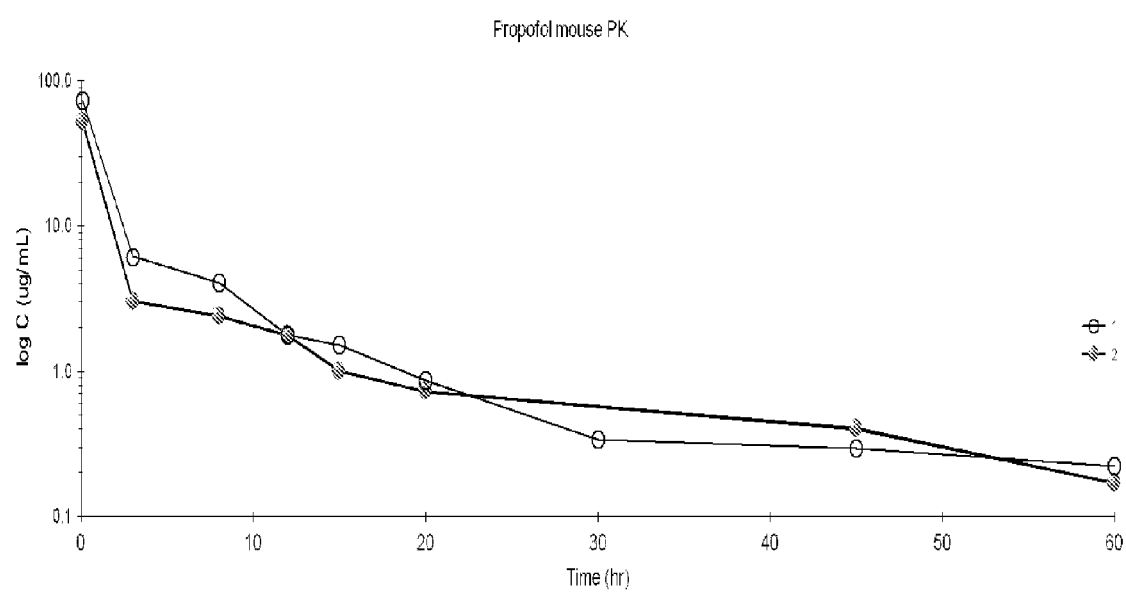
FIG. 2 shows mouse pharmacokinetic profiles of propofol formulations after IV dosing.

FIG. 2 shows mouse PK profiles of propofol formulations with (1) 1% of Propofol in a formulation consisting of 2.5% of OAPDL-12 in saline solution and (2) a commercial product of 1% Propofol The drug was administered intravenously and the dosing strength was 15 mg/kg. From the 2-compartmental calculations, the AUC were 101.6 mg·hr/L with a distribution half-life of 0.68 minutes and elimination half-life of 6.03 minutes for formulation (1) and 71.4 mg·hr/L with a distribution half-life of 0.69 minutes and elimination half-life of 9.3 minutes for the formulation (2), respectively. From the non-compartmental calculations, the AUC were 184.2 mg·hr/L with a half-life of 49.45 minutes for formulation (1) and 133.8 mg·hr/L with a half-life of 19.25 minutes for formulation (2), respectively.

While preferred aspects and embodiments of the present invention have been described, those skilled in the art will recognize that other and further changes and modifications can be made without departing from the spirit of the invention, and all such changes and modifications should be understood to fall within the scope of the invention.

What is claimed is:

1. A pharmaceutical composition for parenteral administration of a pharmaceutical active ingredient, the composition comprising:
    a) an aqueous solution or mixture;
    b) a pharmaceutical active ingredient; and
    c) a solubility enhancer comprising dioleoylglyceroldiethylenetriamine-monomethoxyl polyethylene glycol ether lactobionate:

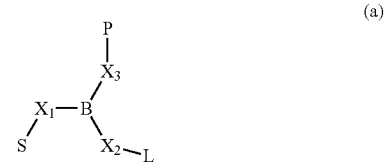

(a)

wherein:
    $X_1$, $X_2$, $X_3$ and $X_l$ are the same or different linking groups comprising at least one of oxy, amide, succinyl and, carbonyl;
    B is a central backbone comprising at least one of glycerol or glycerol-like analogues, polyamine, amino acid, triamine, diethylenetriamine, tetramine, diethylenetetramine, triethylenetetramine, aminoalcohol, and aminopropanediol;
    L is a lipid comprising at least one of diacylglycerol, fatty acids, and bile acids;
    S is carbohydrate comprising saccharide; and
    P is polymer comprising PEG.

2. The pharmaceutical composition of claim 1 comprising the pharmaceutical active ingredient at a concentration between about 0.05 mg/mL and about 50 mg/mL.

3. The pharmaceutical composition of claim 1 comprising a weight ratio of the solubility enhancer to the pharmaceutical active ingredient between about 0.2 and about 25.

4. The pharmaceutical composition of claim 1 comprising a concentration of the polymer-carbohydrate-lipid between about 0.5 percent (w/v) to about 25 percent (w/v).

5. The pharmaceutical composition of claim 1 wherein the pharmaceutical active ingredient is selected from the group consisting of propofol, cisplatin, docetaxel, paclitaxel, posaconazole, voriconazole, and combinations thereof.

6. The pharmaceutical composition of claim 5 wherein the pharmaceutical active ingredient comprises propofol at a concentration in the pharmaceutical composition of between about 0.2 mg/mL to about 25 mg/mL.

7. The pharmaceutical composition of claim 5 wherein the pharmaceutical active ingredient comprises cisplatin at a concentration in the pharmaceutical composition of between about 0.2 mg/mL to about 50 mg/mL.

8. The pharmaceutical composition of claim 5 wherein the pharmaceutical active ingredient comprises docetaxel at a concentration in the pharmaceutical composition of between about 0.2 mg/mL to about 25 mg/mL.

9. The pharmaceutical composition of claim 5 wherein the pharmaceutical active ingredient comprises paclitaxel at a concentration in the pharmaceutical composition of between about 0.2 mg/mL to about 25 mg/mL.

10. The pharmaceutical composition of claim 5 wherein the pharmaceutical active ingredient comprises posaconazole at a concentration in the pharmaceutical composition of between about 0.5 mg/mL to about 40 mg/mL.

11. The pharmaceutical composition of claim 5 wherein the pharmaceutical active ingredient comprises voriconazole at a concentration in the pharmaceutical composition of between about 0.5 mg/mL to about 40 mg/mL.

* * * * *